United States Patent [19]

Reichenberger et al.

[11] Patent Number: 4,928,671

[45] Date of Patent: May 29, 1990

[54] SHOCK WAVE GENERATOR FOR GENERATING AN ACOUSTICAL SHOCK WAVE PULSE

[75] Inventors: Helmut Reichenberger, Eckental; Georg Naser, Zirndorf, both of Fed. Rep. of Germany

[73] Assignee: Siemens Aktiengesellschaft, Berlin and Munich, Fed. Rep. of Germany

[21] Appl. No.: 71,992

[22] Filed: Jul. 10, 1987

[30] Foreign Application Priority Data

Jul. 16, 1986 [DE] Fed. Rep. of Germany ....... 3624069
Apr. 7, 1987 [DE] Fed. Rep. of Germany ....... 3711639

[51] Int. Cl.[5] .............................................. A61B 17/22
[52] U.S. Cl. .............................................. 128/24 A
[58] Field of Search ................. 128/328, 24 A, 660.03

[56] References Cited

U.S. PATENT DOCUMENTS 3,821,510 6/1974 Muncheryan ................... 219/121 L
4,191,189 3/1980 Barkan ................................ 128/328
4,213,344 7/1980 Rose ...................................... 73/620
4,674,505 6/1987 Pauli et al. .......................... 128/328

FOREIGN PATENT DOCUMENTS 0131653 1/1985 European Pat. Off. ............ 128/328
2650624 5/1978 Fed. Rep. of Germany ...... 128/328
3328068 2/1985 Fed. Rep. of Germany ...... 128/328
3447440 7/1986 Fed. Rep. of Germany ...... 128/328

*Primary Examiner*—Ruth S. Smith
*Assistant Examiner*—John D. Zele
*Attorney, Agent, or Firm*—Hill, Van Santen, Steadman & Simpson

[57] ABSTRACT

A shock wave generator has a focusing stage wherein a number of different lenses having respectively different concentrating characteristics are accommodated, and which can be selectively introduced transversely into the path of the shock wave pulse, by linear displacement or by pivoting. The lenses can be alternatively introduced one at a time in one embodiment, or in a second embodiment more than one lens can be simultaneously introduced to achieve a concentrating characteristic resulting from a combination of lenses. For further adjustment and flexibility, the shock wave generator is provided with at least two capacitors for selectively varying the amount of discharge energy used to trigger the shock wave. The approach path between the membrane which generates the shock wave and the lens can also be varied. By combining variations in the discharge energy, the length of the approach path, and the type of lens, a wide range of operating conditions are available so that operation of the shock wave generator can be adapted from patient to patient in accord with the best suited treatment.

20 Claims, 4 Drawing Sheets

SHOCK WAVE GENERATOR FOR GENERATING AN ACOUSTICAL SHOCK WAVE PULSE

BACKGROUND OF THE INVENTION

1. Field of the Invention

The present invention is directed to a shock wave generator for generating an acoustical shock wave pulse, and in particular to such a shock wave generator wherein the shock wave pulse is generated by a membrane which is rapidly repelled by a coil, and which has an acoustic lens for concentrating the shock wave.

2. Description of the Prior Art

A shock wave generator is disclosed in German OS No. 33 28 051 (corresponding to the U.S. Pat. No. 4,679,505) of the type generally referred to as a "shock wave tube" for lithotripsy. The shock wave generator includes an electrical coil and a metal membrane separated therefrom by an insulating foil. When a capacitor is suddenly discharged through the coil, electromagnetic forces are generated which cause the metal membrane to rapidly repelled from the coil resulting in the emission of a shock wave pulse. An approach path or fluid path is provided adjacent to the metal membrane through which the shock wave pulse travels along a path to a patient. An acoustic lens is disposed in the approach path which operates as a focusing means to concentrate the incoming shock wave at the focus of the lens, which is preferably coincident with the position of a calculus to be disintegrated in the patient.

In practice, different treatment requirements arise from patient to patient. Such treatment conditions can vary, for example, in dependence on the type and size of the calculus to be disintegrated, the geometry of the calculus (for example, round or oblong), the distance of the calculus from the skin surface (defined by the position of the stone or the physical bulk of the patient), and on the number of calculi. In addition to these different initial conditions due to different patients, different conditions are also present as a result of the progress of the shock wave treatment. For example, during an initial treatment relatively large fragments of the calculus are first generated in a relatively wide effective zone, and these fragments must then be comminuted into smaller particles in a subsequent treatment in a more narrowly prescribed effective zone.

In order to adapt the shock wave generator to these different treatment conditions, it has been heretofore necessary to either vary the discharge voltage of the capacitor, or to vary the distance of the focusing means from the skin of the patient. These measures are not sufficient to fully adapt the shock wave generator to the large number of different treatment conditions in a satisfactory manner.

SUMMARY OF THE INVENTION

It is an object of the present invention to provide a shock wave generator of the type described above which can be easily adapted to a plurality of different treatment conditions, and which thereby permits more effective lithotripsy treatment.

The above object is achieved in accordance with the principles of the present invention in a shock wave generator having a number of lenses with different concentrating characteristics, and means for alternately introducing one of the lenses into the path of the shock wave pulse, or simultaneously introducing a number of the lenses into the shock wave path. The adaptability of the shock wave generator is further increased by providing means for varying the approach path between the shock wave emission surface (the membrane) and the focusing means (the lens). Further variability in the operation of the shock wave generator is achieved by providing a plurality of capacitors which are discharged in various combinations to provide different discharge durations and/or energies for the generation of shock wave pulse.

With respect to the variation of the capacitance, tests have shown that in a shock wave tube having a diameter of 12 cm, the duration of the discharge current can be shortened from 5 μs to 3.5 μs given reduction of the capacitance from, for example, 1 μf to 0.5 μf. An advantageous result is that the emitted shock wave pulse is correspondingly shorter in duration, and the pulse is thus attenuated to an increased degree after focusing. A shorter focused pulse has a lower energy content given comparable pressure amplitude and has a more restricted effective zone. Such a shorter focus pulse can be used for local erosion of the calculus, instead of a shattering thereof.

As used herein, the term "concentrating characteristic" in conjunction with the acoustic lenses relates both to the focal length of the lens and to the type of lens. For calculi close to the skin, or calculi in children, the use of a lens having a short focal length and a large aperture angle produces a higher focusing degree, i.e., a smaller focus area or volume effective for disintegration, given reduced acoustic power, than a lens having a long focal length and a small aperture angle, which generates a larger effective focus volume and thus has a larger focusing degree. An overall more gentle treatment is achieved using a high focusing degree. Calculi which lie deeper within the patient, for example in more corpulent patients, by contrast, require a lens having a longer focus, so that an optimum effect can be achieved. The use of cylindrical lenses (for example, bi-cylindrical or spherical/cylindrical) produces advantages in the treatment of large calculi or in the case of a plurality of calculi disposed side-by-side, which are to be treated simultaneously.

The selection of capacitance, lens and/or approach path in combination with a suitable selection of the capacitor voltage and the distance of the focusing means from the skin of the patient can be revised as needed from patient to patient, or during the progress of the treatment for one patient.

Another object of the present invention is to provide an adaptable shock wave generator having a simple format. In particular, it is an object to provide a means which is structurally and operationally simple for modifying the focal length. Another object is to maintain the shock wave generator in a compact and relatively narrow structure.

These further objects are achieved in a first embodiment wherein a plurality of lenses having different concentrating characteristics are provided for individual introduction into the path of the shock wave pulse. The lenses are mounted on a common carriage, and the carriage can be either linearly displaced in a guide disposed transversely relative to the path of the shock wave pulse, or can be pivoted so as to bring one of the lenses into the path.

In a further embodiment, the same types of displacement means can be used to introduce more than one lens into the path of the shock wave pulse in series so as to achieve concentrating characteristics which are a combination of the characteristics of a number of lenses.

DESCRIPTION OF THE PREFERRED EMBODIMENTS

Figure 1:
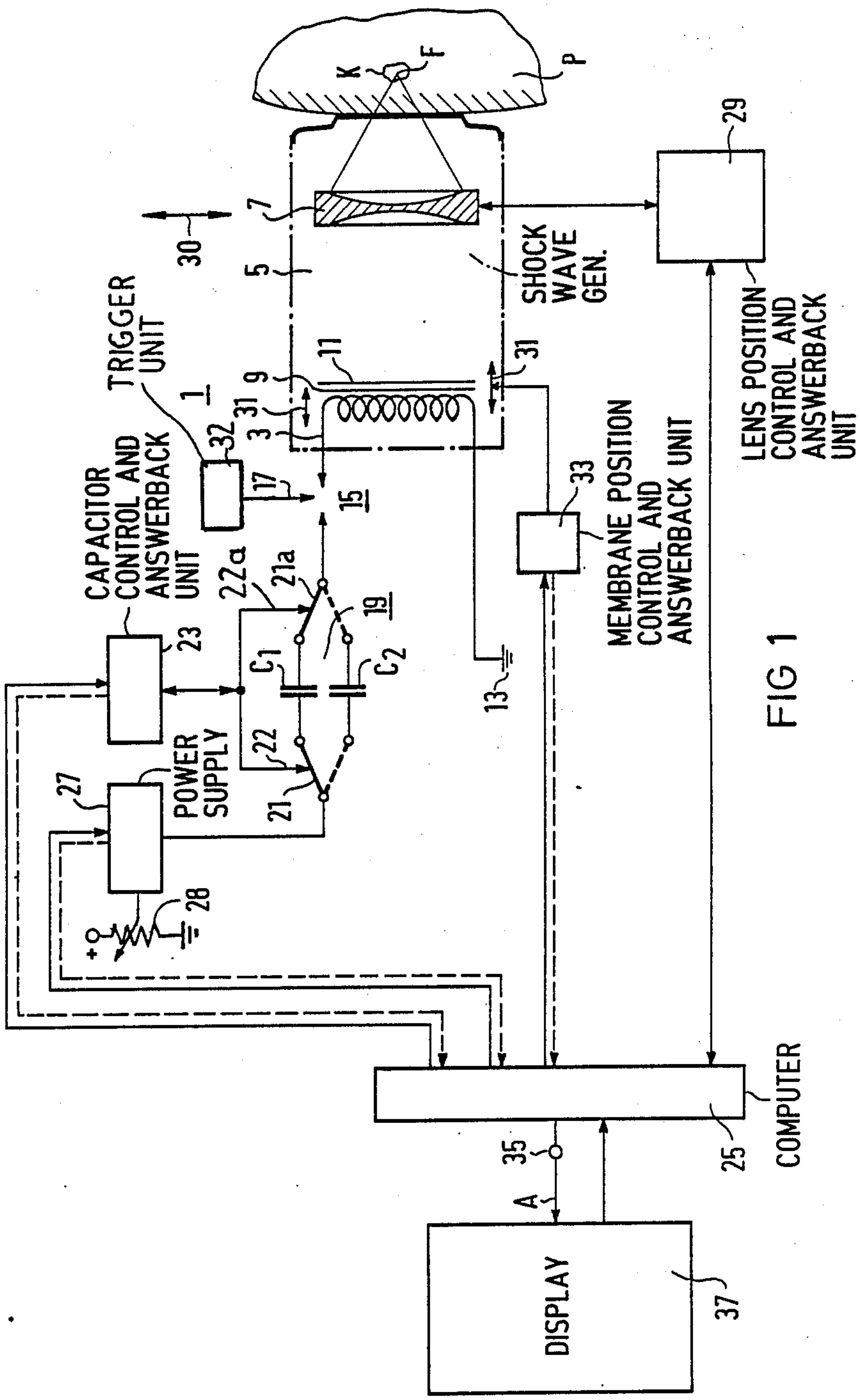
FIG. 1 is a schematic block diagram of a first embodiment of a shock wave generator constructed in accordance with the principles of the present invention.

In the drawings and in the following description, identical elements appearing in different drawings have been provided with the same reference symbol.

A shock wave generator 1 is shown in FIG. 1 of the type referred to as a "shock wave tube." The shock wave generator 1 includes a flat coil 3, an approach or fluid path 5, and a focusing means 7. A membrane 11 of bronze or copper is disposed preceding the flat coil 3, and separated therefrom by an insulating foil 9. The approach path 5 between the membrane 11 and focusing means 7 is filled with a coupling agent, which is a shock wave conducting medium, such as, for example, water.

When the flat coil 3 is charged with a voltage pulse, the membrane 11 is suddenly repelled due to electromagnetic forces. An acoustic shock wave pulse is thereby generated in the approach path 5. This shock wave pulse, which is essentially planar within the approach path 5, is focused to a focus F by the focusing means 7. The focus F is disposed in the region of a calculus K in the body of a patient P to be treated.

One end of the flat coil 3 is connected to a reference potential 13, such as ground, and the other end terminates as one electrode of a spark gap 15. The spark gap 15 is provided with an auxiliary electrode 17 for triggering. The auxiliary electrode 17 is driven by a trigger unit 32 of the type well-known to those skilled in the art. The spark gap 15 is also connected to a capacitor bank 19. In the schematically illustrated exemplary embodiment, the capacitor bank 19 includes a capacitor $C_1$ and a capacitor $C_2$. The capacitor $C_1$, for example, may have a capacitance of 1 $\mu$f and the capacitor $C_2$ may have a value of 0.5 $\mu$f. By means of switches 21 and 21*a*, either the capacitor $C_1$ or the capacitor $C_2$ is connected to the spark gap 15. Alternatively, the capacitor bank 19 may consist of a plurality n of different capacitors Ci, where i=1 through n, with one of these n capacitors being selectively connectable to the spark gap 15. In a further alternative, the capacitor bank 19 may consist of a plurality of identical capacitors Ci, which can be connected in parallel or in series by suitable switching means, so that different capacitances derive at the output. Lastly, a mixed embodiment of different capacitors Ci which can be selectively connected in parallel and/or in series sub-circuits is also possible.

The control contact 22 of the switch 21 and the control contact 22*a* of the switch 21*a* are connected to a capacitor control and answerback unit 23, which is connected to a computer 25 for identifying a parameter of the shock wave pulse such as, for example, the pressure thereof, the pulse duration, or the focus geometry. The control and answerback unit 23 sets a desired capacitance at the capacitor bank 19.

For supplying the capacitor bank 19 with energy, the switch 21 is connected to a power supply 27 having an adjustable output voltage. The power supply 27 is also connected to the computer 25. The output voltage of the power supply 27 can be selected by a setting element 28, for example a potentiometer.

The focusing means 7 includes a plurality of lenses which can be selectively introduced into the path of the shock wave pulse. A lens position control and answerback unit 29 operates to shift (in one embodiment) or rotate (in another embodiment) the plurality of lenses and provides a signal to the computer 25 identifying the selected lens. The possibility of linear displacement of the different lenses transversely relative to the longitudinal axis of the shock wave tube is indicated by the double arrow 30.

The possibility of displacing the flat coil 3, the insulating foil 9 and the membrane 11 so as to vary the length of the approach path 5 is schematically indicated by the double arrow 31. A structural implementation of means for changing the approach path 5 is shown in greater detail in FIG. 2. The position of the membrane 11 is controlled and identified by a membrane position control and answer back unit 33, which is controlled by the computer 25 and which, provides a signal to the computer 25 indicating the position of the membrane 11 and thus the length of the approach path 5.

The computer 25 thus has four inputs to which respective status signals identifying the capacitance selection, the capacitor voltage, the lens selection and the length of the approach path are supplied. The computer 25 uses the information from these signals to form an output signal A, which corresponds to the resulting value of a parameter of the shock wave pulse. Such a parameter may, for example, be the peak pressure of the shock wave pulse, the pulse duration, or the focus geometry. The computer 25 has an output 35 at which the output signal A is forwarded to a display means 37. The display means 37 can be a means for displaying an x-ray or ultrasound image in the examination area of the patient P, in which case the values of the parameters of the shock wave pulse are mixed into the image.

An advantage of the exemplary shock wave generator 1 shown in FIG. 1 is the large variation possibility in its operating data which is afforded. By varying the capacitance of the capacitor bank 19, the duration and amplitude of the shock wave pulse as well as the extend of the focus zone, for example the $-6$ dB zone relative to the pressure maximum, can be modified. The length of the approach path 5 is varied by displacing the shock wave emission surface, i.e., by shifting the membrane 11 in the exemplary embodiment. The steepness of the shock wave pulse at the location of the focusing means 7 can thus be continuously varied. The possibility of replacing one focusing means 7 (lens) with another focusing means, indicated by the double arrow 30, is especially advantageous. For example, operation at the beginning of a treatment for a large calculus K can be undertaken using a cylindrical lens having a line focus. At a subsequent point in the treatment, a shift can be made to use a spherical lens having a punctiform focal region in order to achieve better disintegrating action in view of the now smaller fragments.

Figure 2:
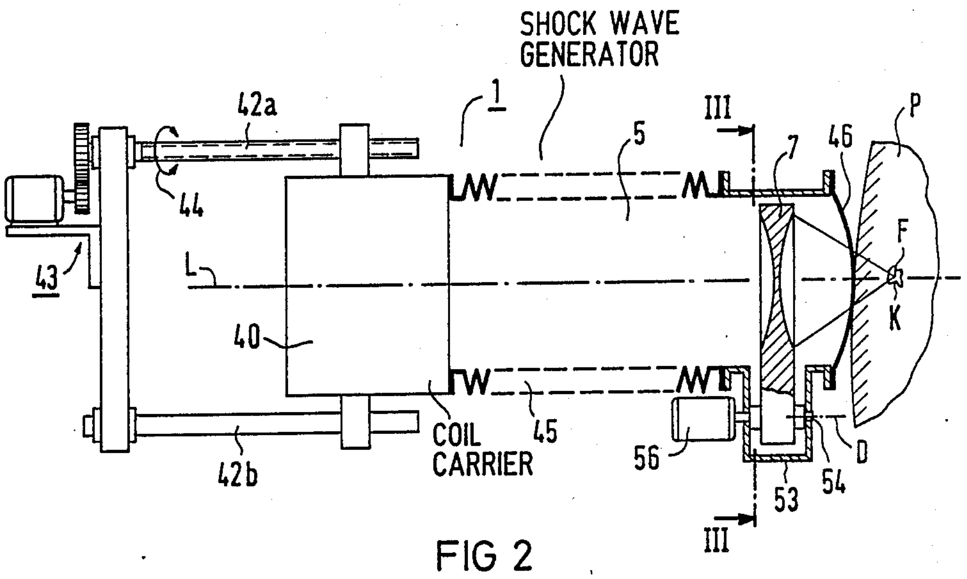
FIG. 2 is a side view, partly in section, showing means for adjusting the approach path of the shock wave generator in the embodiment of FIG. 1.

A structural embodiment of a means for modifying the length of the approach path 5 and for interchanging the focusing means 7 is shown in FIG. 2. In this embodiment, the flat coil 3, the insulating foil 9 and the membrane 11 are contained within a coil carrier 40, and are thus not shown in detail. The coil carrier 40 is secured to a plurality of rods 42*a* and 42*b*, of which at least one is threaded (such as the rod 42*a*), and which are held by a frame 43. By rotating the threaded rod 42*a* as indicated by the curved double arrow 44, the coil carrier 40 and thus the emission surface of the shock wave generator (the membrane 11), is shifted along the longitudinal axis L of the shock wave generator 1. When the focusing means 7 is situated at a prescribed coordinate on the longitudinal axis L, the length of the approach path 5 is varied by shifting the coil carrier 40 via the threaded rod 42*a*. A cylindrical jacket limiting the approach path 5 may be in the form of accordion bellows 45, so that length modifications can be easily accommodated.

A re-adjustment of the shock wave generator 1 is not necessary for different patients P. Because the focusing means 7 is stationary, the arrangement of the focusing means 7, the focal point F and the calculus K is unchanged. A membrane 46, which terminates the shock wave generator and serves to couple the focused shock wave to the patient, also lies against the patient P unchanged when the coil carrier 40 is shifted.

Figure 3:
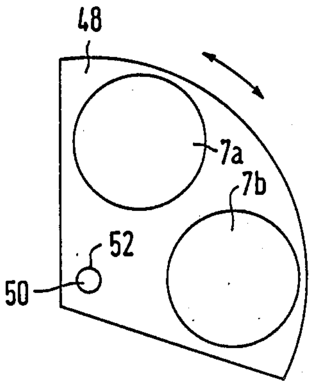
FIG. 3 is a plane view of a carriage for use in the embodiment of FIG. 1 having a plurality of lenses.

In combination with FIG. 2, a means for selecting and interchanging the focusing means 7 is shown in FIG. 3. In this embodiment, two lenses 7*a* and 7*b* are mounted on a mount 48 which is a segment of a circle. The lenses 7*a* and 7*b* have respectively different concentrating characteristics (focal length, focal region). The mount 48 has a pivot point 50, and is rotatable at the pivot point 50 around an axis D which is parallel to the longitudinal axis L. The pivot point 50 is coincident with the center axis of a bore 52 in the housing 53 of the shock wave generator 1. A pin 54 is received in the bore 52, the central axis of the pin 54 proceeding parallel to the longitudinal axis L of the shock wave generator 1, and being coincident with the rotational axis D around which the mount 48 is rotatable. The pin 54 is connected to the shaft of a motor 56. Positioning of the lenses 7*a* and 7*b*, and the generation of a signal indicating which lens 7*a* or 7*b* is in the path of the shock wave, are undertaken by the motor 56.

It is also possible to design the mount 48 as a complete circular disk having more than two focusing means or lenses 7.

In another embodiment, the mount may be in the form of a slide or carriage such that the lenses are introduced into the path of the shock wave pulse by linear displacement, similar to the manner by which slides are introduced into the light beam in a slide projector. Such embodiments are shown in FIGS. 4 through 8.

Figure 4:
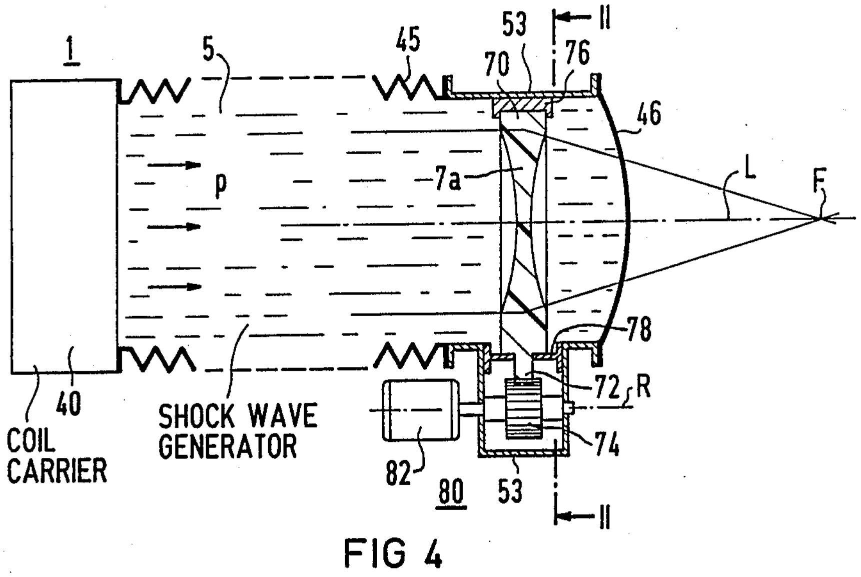
FIG. 4 is a side view, partly in section, showing a further embodiment for displacing the lens carriage.
Figure 5:
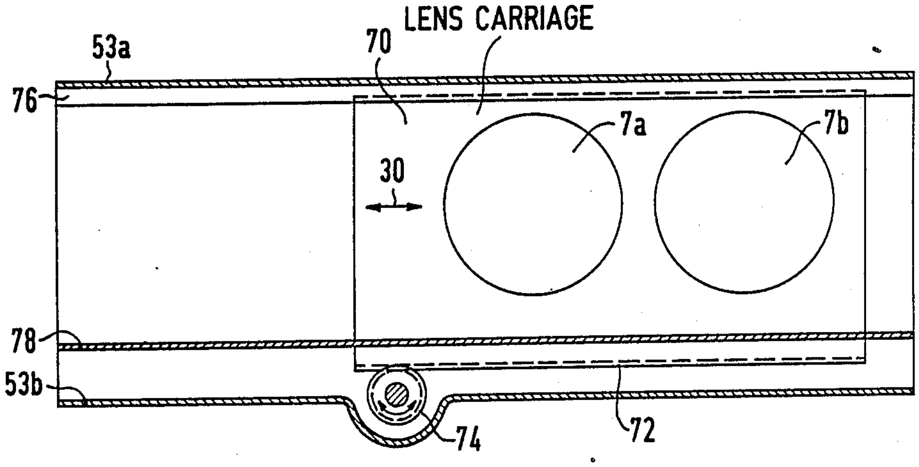
FIG. 5 is a plane view of the lens carriage, and means for mounting the carriage, in the embodiment of FIG. 4.

As shown in FIGS. 4 and 5, a shock wave generator 1 is provided which again may be a "shock wave tube" of the type described in German OS No. 33 28 051 (corresponding to U.S. Pat. No. 4,674,505) for lithotripsy. A closed coil carrier 40, containing a flat coil, an insulating foil and a membrane, is connected to the approach path 5 filled with a coupling fluid, limited by an accordian bellows 45, a housing 53, and a coupling membrane 46 at the end thereof closer to the patient. A planar shock wave pulse p is triggered in the coil carrier 40 and is focused along the longitudinal axis L to a focus F which is coincident with the position of the calculus to be disintegrated.

One of two lenses 7*a* or 7*b* is provided as the focusing means for focusing the shock wave to the focus F. One of the lenses can be optionally inserted into the approach path 5 of the shock wave (having a longitudinal axis L). The lenses 7*a* and 7*b* are disposed side-by-side on a common carrier, slide or carriage 70, which may be rectangular. The lenses 7*a* and 7*b* can be shifted transversely relative to the longitudinal axis L by the carriage 70. The lenses 7*a* and 7*b* may be either applied to the carriage 70, for example being screwed or glued thereto, or may be integrated therein, for example, cast in one part.

The carriage 70 is provided with teeth 72, for example in the form of a horizontal toothed rack, at its lower side. A gear wheel 74 received in the housing 53 meshes with the teeth 72. The carriage 70 is guided transversely relative to the longitudinal axis L by horizontal top and bottom guides 76 and 78, attached to the housing 53. The carriage 70 can be adjusted between two positions by a drive system 80 including an electrical motor 82 which rotates the gear wheel 74 about a rotational axis R which is parallel to the longitudinal axis L. The resulting linear reciprocal motion is identified by the double arrow 30. Activation of the electric motor 82 thus positions either the first lens 7*a* or the second lens 7*b* in the approach path 5 of the shock wave pulse p. The desired focal length can be set in this manner, i.e., the distance between the shock wave generator 1 and the focus F can be varied by appropriate lens selection.

Figure 6:
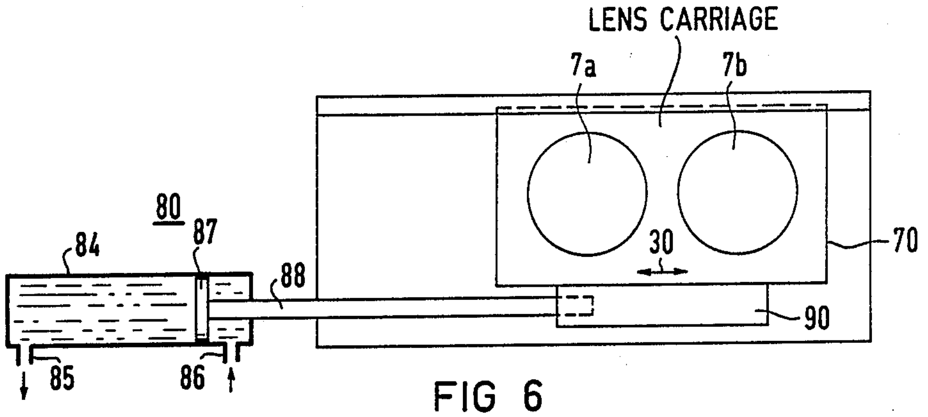
FIG. 6 is a plane view of a further embodiment for displacing the lens carriage in the embodiment of FIG. 4.

FIG. 6 corresponds to the embodiment of FIG. 5, however, in FIG. 6 a hydraulic cylinder 84 is provided as the drive system 80. The hydraulic cylinder 84 is driven with hydraulic fluid via control connections 85 and 86. A piston 87 acts on a rod 88 having a lower connecting member 90 rigidly connected to the common carriage 70. Again, the resulting reciprocal motion is indicated by the double arrow 30, and is achieved dependent on the direction of flow of the hydraulic fluid.

Figure 7:
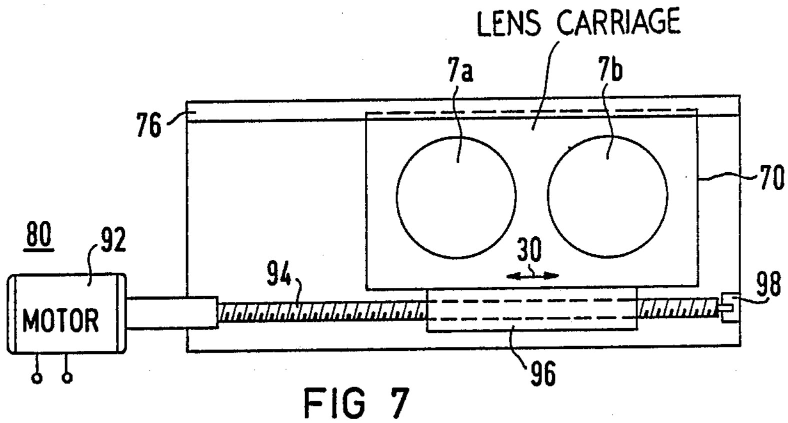
FIG. 7 is a plane view of another embodiment for displacing the lens carriage in the embodiment of FIG. 4.

Another embodiment is shown in FIG. 7 wherein the drive system 80 is in the form of a motor 92 having a drive shaft (not shown) connected to a threaded rod 94 which is received in an extended nut 96. The nut 96 is attached to the bottom of the carriage 70. The opposite end of the threaded rod 94 is received in a journal 98. When the shaft of the motor 92 is rotated, thereby rotating the threaded rod 94, the carriage 70 together with the lenses 7*a* and 7*b* is linearly adjusted in the direction of the double arrow 30.

Figure 8:
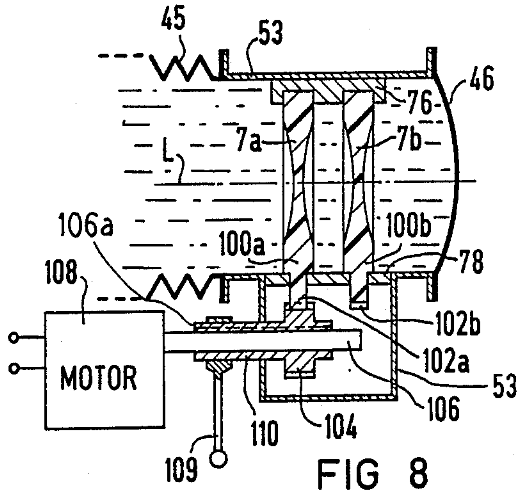
FIG. 8 is a side sectional view of a portion of the shock wave generator in the embodiment of FIG. 4\ with a plurality of lenses disposed in series in the shock wave pulse path.

In the embodiments of FIGS. 4 through 7, only one of the lenses 7*a* or 7*b* was situated in the acoustic approach path 5 of shock wave travel. In the embodiment of FIG. 8, however, more than one lens can be disposed in this path. In this embodiment, either the first lens 7*a*, the second lens 7*b*, or both lenses in series, can be optionally situated in the path 5. The two lenses 7*a* and 7*b* may have the same focal length, however, in practice it is preferable if the lenses have different focal lengths, for example, 15 cm and 12 cm, respectively. When the two lenses having such focal lengths are used in combination, a focal length of approximately 7 cm results. The lenses are again introduced in a horizontal direction.

In the embodiment of FIG. 8, the lenses *7a* and *7b* are optionally introduceable into the approach path 5 in the proximity of the membrane 46 either individually or in combination by means of upper and lower transverse guides 76 and 78.

As shown in the drawing, the lenses *7a* and *7b* are disposed at a distance from each other, and are double concave lenses. The lenses may, however, be planar-concave such that when arranged in series (i.e., when both lenses are simultaneously introduced), the respective planar sides of the lenses have a minimum spacing which can be selected as small as desired down to virtual contact, in which case the lenses will be separated only by a thin water film.

As shown in FIG. 8, both lenses *7a* and *7b* are carried on respective carriages **100*a* and 100*b* which slide in the transverse guides 76 and 78. The carriage 100*a* has teeth 102*a* on a lower edge thereof, and the carriage 100*b* has teeth 102*b* on the bottom thereof, again in the form, for example, of a toothed rack. The teeth 102*a* and 102*b* are actuated by a drive pinion 104 which is mounted on the drive shaft 106 having a spline 106*a* of an electric motor 108. In the position shown in FIG. 8, the drive pinion 104 meshes with the teeth 102*a***.

When the first lens *7a* is to be introduced into the shock wave path L or is to be removed therefrom, the motor 108 is driven so as to rotate the shaft 106 in the appropriate direction. When the second lens *7b* is to be introduced or removed from the path L, the drive pinion 104 is first disengaged from the teeth **102*a* and is shifted so as to mesh with the teeth 102*b* of the second carriage 100*b*. This shift is effected by means of a lever 109 secured to a sleeve 110 which is in turn mounted on the drive shaft 106**, or which may be integrally formed therewith.

It is also possible to use separate drive systems for each of the lenses *7a* and *7b*, as in the embodiment of FIGS. 4 and 5, by means of separate teeth and a separate pinion for each lens, so that one or both of those lenses can be introduced in the shock wave path. Another modification can be undertaken similar to the embodiment of FIG. 7, by using separate threaded rods and separate nuts for each lens carrier.

It is also possible to modify the embodiment of FIG. 8 to employ a rotational carriage for the lenses *7a* and *7b* instead of the linearly displaceable carriage. The lenses would then be rotated into the shock wave path L similar to the manner shown in FIGS. 2 and 3. One motor and a shifting means can be used, or two separate motors could be used.

In comparison with the embodiments shown in FIGS. 4 through 7, the series arrangement of the two lenses *7a* and *7b* and their respective carriages **100*a* and 100*b*** has the advantage that lateral space is saved while the range of variation in the focal length is increased.

Although modifications and changes may be suggested by those skilled in the art it is the intention of the inventors to embody within the patent warranted hereon all changes and modifications as reasonably and properly come within the scope of their contribution to the art.

We claim as our invention:

1. A shock wave generator comprising:

means for generating a shock wave pulse having a path of travel;

a plurality of acoustic lenses having respectively different concentrating characteristics;

means for holding said lenses; and means for moving said means for holding in a direction transverse to said path of travel for selectively introducing at least one of said lenses into said path of said shock wave pulse from a standby position out of said path of said shock wave pulse.

2. A shock wave generator as claimed in claim 1, wherein said means for moving is a means for alternately moving one of said lenses transversely into said path of said shock wave pulse.

3. A shock wave generator as claimed in claim 1, wherein said means for moving is a means for simultaneously moving more than one of said lenses in series transversely into said path of said shock wave pulse.

4. A shock wave generator as claimed in claim 1, wherein said means for holding comprises a carriage on which said lenses are mounted side-by-side, and wherein said means for moving comprises means for linearly displacing said carriage transversely to said path to position one of said lenses in said path.

5. A shock wave generator as claimed in claim 4, wherein said means for linearly displacing comprises:

a gear and a means for rotating said gear about an axis parallel to said path; and a plurality of teeth disposed on one side of said carriage meshing with said gear.

6. A shock wave generator as claimed in claim 4, wherein said means for linearly displacing comprises:

a threaded rod and means for rotating said threaded rod; and a nut receiving said threaded rod mounted on a side of said carriage.

7. A shock wave generator as claimed in claim 4, wherein said means for linearly displacing comprises:

a hydraulic cylinder having two spaced fluid ports therein; and a piston having a piston head disposed between said ports and a piston rod attached to said carriage.

8. A shock wave generator as claimed in claim 1, wherein said plurality of lenses includes at least a first lens and a second lens, and wherein said means for holding comprises:

a first carriage on which said first lens in mounted and having a driveable engagement means thereon, and a second carriage on which said second lens is mounted and having a driveable engagement means thereon; and wherein said means for moving comprises:

a drive shaft having a driving engagement means thereon engageable with said driveable engagement means on each of said first and second carriages, means for rotating said drive shaft, and means for shifting the position of said drive shaft to engage said driving engagement means thereon with one of said driveable engagement means to linearly displace one of said carriages transversely to said path.

9. A shock wave generator as claimed in claim 8, further comprising means for slideably mounting said first and second carriages in series in said path.

10. A shock wave generator as claimed in claim 1, wherein said means for holding comprises a carrier on which said lenses are mounted, said carrier being shaped as a segment of a circle, and wherein said means for moving comprises means for rotating said carrier about an axis parallel to said path to position one of said lenses in said path.

11. A shock wave generator as claimed in claim 1, wherein said means for generating said shock wave pulse has a shock wave emission surface, and an approach path for said shock wave pulse defined by the distance between said shock wave emission surface and a lens in said plurality of said lenses closest thereto, and means for varying the length of said approach path.

12. A shock wave generator as claimed in claim 11, wherein said means for varying the length of said approach path is a means for changing the location of said shock wave emission surface along said shock wave pulse path of travel relative to said closest lens.

13. A shock wave generator as claimed in claim 1, wherein said means for generating said shock wave pulse includes means for varying the duration of said shock wave pulse.

14. A shock wave generator as claimed in claim 1, wherein said means for generating said shock wave pulse includes a coil and an electrically conducting membrane spaced therefrom and means for rapidly applying a voltage across said coil to repel said membrane therefrom.

15. A shock wave generator as claimed in claim 14, wherein said means for applying a voltage includes a capacitor bank having a plurality of capacitors, and switching means for selectively connecting different combinations of said capacitors to said coil.

16. A shock wave generator as claimed in claim 1, wherein said means for generating said shock wave pulse includes means for varying the energy of said shock wave pulse.

17. A shock wave generator as claimed in claim 1, wherein each of said lenses in said plurality of lenses has a different focal region.

18. A shock wave generator as claimed in claim 1, wherein each of said lenses in said plurality of lenses has a different focal length.

19. A shock wave generator comprising:

means for generating a shock wave pulse having a path of travel proceeding from a shock wave emission surface;

a plurality of acoustic lenses having respectively different concentrating characteristics;

a holder in which said acoustic lenses are mounted;

means for moving said holder in a direction transverse to said path of travel for selectively introducing at least one of said lenses into said path of said shock wave pulse;

an approach path through which said shock wave travels defined by the distance between said shock wave emission surface and a closest of said lenses in said path of said shock wave;

means for varying the length of said approach path;

means for varying the duration of said shock wave pulse; and means for varying the amplitude of said shock wave pulse.

20. A shock wave generator comprising:

means for generating a shock wave pulse having a path of travel;

a plurality of acoustic lenses having respectively different concentrating characteristics;

a holder in which said plurality of acoustic lenses are mounted in a non-overlapping fashion; and means for moving said holder to selectively position one of said lenses in said holder in said path of said shock wave pulse.

* * * * *